(12) United States Patent
Natbony

(10) Patent No.: US 10,835,633 B2
(45) Date of Patent: Nov. 17, 2020

(54) SECURE TAMPON

(71) Applicant: THINK DO IT, Marietta, GA (US)

(72) Inventor: Suzanne Raina Natbony, Los Angeles, CA (US)

(73) Assignee: THINK DO IT, Marietta, GA (US)

( * ) Notice: Subject to any disclaimer, the term of this patent is extended or adjusted under 35 U.S.C. 154(b) by 456 days.

(21) Appl. No.: 15/648,380

(22) Filed: Jul. 12, 2017

(65) Prior Publication Data

US 2019/0015543 A1 Jan. 17, 2019

Related U.S. Application Data

(60) Provisional application No. 62/379,404, filed on Aug. 25, 2016.

(51) Int. Cl.
*A61F 13/20* (2006.01)
*A61F 13/34* (2006.01)
*A61L 15/58* (2006.01)
*A61L 15/28* (2006.01)
*A61F 13/58* (2006.01)
*A61L 15/42* (2006.01)

(52) U.S. Cl.
CPC ............ *A61L 15/58* (2013.01); *A61F 13/202* (2013.01); *A61F 13/204* (2013.01); *A61F 13/34* (2013.01); *A61F 13/58* (2013.01); *A61L 15/28* (2013.01); *A61L 15/42* (2013.01)

(58) Field of Classification Search
CPC ...... A61F 13/20; A61F 13/202; A61F 13/204; A61F 13/34
See application file for complete search history.

(56) References Cited

U.S. PATENT DOCUMENTS

| 3,037,506 A | * | 6/1962 | Penksa | A61F 13/2051 604/385.18 |
| 3,948,257 A | * | 4/1976 | Bossak | A61F 13/2051 604/359 |
| 5,350,371 A | * | 9/1994 | Van Iten | A61F 13/2051 604/378 |
| 6,312,419 B1 | * | 11/2001 | Durel-Crain | A61F 13/34 604/385.18 |
| 6,679,868 B2 | * | 1/2004 | Kostadimas | A61F 13/34 604/385.18 |
| 2002/0068918 A1 | * | 6/2002 | Durel-Crain | A61F 13/34 604/385.18 |

* cited by examiner

*Primary Examiner* — Catharine L Anderson

(57) ABSTRACT

The present invention relates to novel and secure tampons that overcome the problems associated with conventional non-secure tampons, and methods of using the novel and secure tampons.

4 Claims, 3 Drawing Sheets

150    151

210

200

180

SECURE TAMPON

CROSS REFERENCE TO RELATED APPLICATION

This patent application claims priority to U.S. Provisional Patent Application Ser. No. 62/379,404, filed Aug. 25, 2016.

BACKGROUND

Field of the Invention

The present invention relates to novel and secure tampons that overcome the problems associated with conventional non-secure tampons, and methods of using the novel and secure tampons.

Background of the Invention

Menstruation products compose an estimated 15 billion dollar market. The average woman uses about 10,000 sanitary products during her lifetime. Most women use tampons and women younger than 41 are far more likely to use them. Sometimes women wear both a tampon and a pad at the same time, for extra protection. About one in four women in perimenopause (ages 48 to 54) use tampons and/or pads between their periods. Tampons, which have been around since the 1930s, are the most popular choice of feminine protection for women younger than 41. Women often choose tampons for greater physical freedom during their period. Women usually change tampons at least every four to eight hours, typically using the least absorbent type to manage menstrual flow. Tampons are not recommended in between periods. There was a connection between conventional, non-secure superabsorbent tampons and an outbreak of toxic shock syndrome (TSS) in the 1980s, and these "hyper absorbable" tampons were taken off the market. In addition to pads and tampons, menstruation cups and Thinx® panties are other types of menstruation products. In the 1980s, Always® became an industry leader by introducing "wings" on pads. Many women prefer pads with wings over pads without wings. However, with conventional non-secure tampons, women sometimes forget about the tampon and actually "lose" the tampon inside of them, which can be very dangerous. Losing a tampon is associated with many significant problems for women, including but not limited to toxic shock syndrome (TSS), a life-threatening disease. Further, many women and, especially younger girls, will not wear tampons or avoid them because of not only the fear of a "lost tampon," but also the association with TSS.

Most conventional, non-secure tampons have a string for removal; however with conventional, non-secure tampons there is no adhesive element that is attached to the string. Therefore, with conventional, non-secure tampons, the string is sometimes lost, for instance when the string gets stuck or trapped or lodged within the vagina. This loss of the string is problematic and dangerous to the woman's health. The use of a conventional, non-secure tampon is therefore often associated with many significant problems for women, including but not limited to toxic shock syndrome (TSS), a life-threatening disease. In addition to TSS, the use of conventional, non-secure tampons can also cause other serious problems including, but not limited to, urinary tract infections, urogenital infections, vaginal ulcers and unwanted mucosal changes, each of which can be very detrimental. Lost tampons can also cause anxiety in women as treatment for lost tampons can occur not only with an OBGYN, but also at emergency rooms and urgent care centers.

Therefore, while many non-secure, conventional tampons have strings attached, these non-secure, conventional tampons pose significant problems for women since the string is often lost or gets lodged in the vagina.

There is therefore a long-felt, significant and unmet need in the art for improved, secure tampons and methods of using secure tampons.

Additional aspects of the invention will become apparent in view of the following description and associated figures.

SUMMARY OF THE INVENTION

Certain embodiments of the present invention provide a secure tampon, comprising an absorbent object which is securely attached to at least one or more connector elements, and further wherein the one or more connector elements are safely and securely attached to at least one or more adhesive elements.

Other embodiments of the present invention provide a secure tampon, wherein the at least one or more connector elements comprise any type of safe and non-toxic string, thread, filament, fiber, microfiber, yarn or other type of safe and non-toxic connective element.

Other embodiments of the present invention provide a secure tampon, wherein the at least one or more adhesive elements securely and reversibly attach to at least one area of the tampon wearer's body.

Other embodiments of the present invention provide a secure tampon, wherein the at least one or more adhesive elements comprise any type of safe and non-toxic tape, adhesive material, waterproof tape, medical adhesive tape, pressure sensitive adhesive tape, surgical tape, paper tape, or any combination thereof.

Other embodiments of the present invention provide a secure tampon, wherein the at least one or more adhesive elements comprise cloth, waterproof material, paper, pressure-sensitive tape, micropore adhesive material, or any combination thereof.

Other embodiments of the present invention provide a secure tampon, wherein the one or more adhesive elements securely and reversibly attach to any area of skin surrounding the vagina, any part of the leg or legs, inner thigh, or any area of the skin covering the pubic bone.

Other embodiments of the present invention provide a secure tampon, wherein the absorbent object is made of a material selected from the group consisting of cotton, rayon, and a blend of cotton and rayon.

Other embodiments of the present invention provide a self-assembled secure tampon comprising an absorbent object which is already securely attached to at least one or more connector elements, and further wherein the one or more connector elements are safely and securely attached to at least one or more adhesive elements.

Other embodiments of the present invention provide a secure tampon comprising at least one adhesive means for attaching the secure tampon to at least one area of a woman's body.

Other embodiments of the present invention provide a secure tampon, wherein the means for attaching the secure tampon to at least one area of a woman's body comprises the use of tape or other adhesive material that is attached to at least one or more connector elements.

Other embodiments and further details regarding various aspects of the present invention are set forth in the following description and claims. It is to be understood that the invention is not limited in its application to the details set forth in the following description and claims, but is capable of other embodiments and of being practiced or carried out in various ways.

BRIEF DESCRIPTION OF THE DRAWINGS

These and/or other aspects and advantages of the invention will become apparent and more readily appreciated from the following description of the embodiments, taken in conjunction with the accompanying drawings of which.

DESCRIPTION OF PREFERRED EMBODIMENTS

Figure 1:
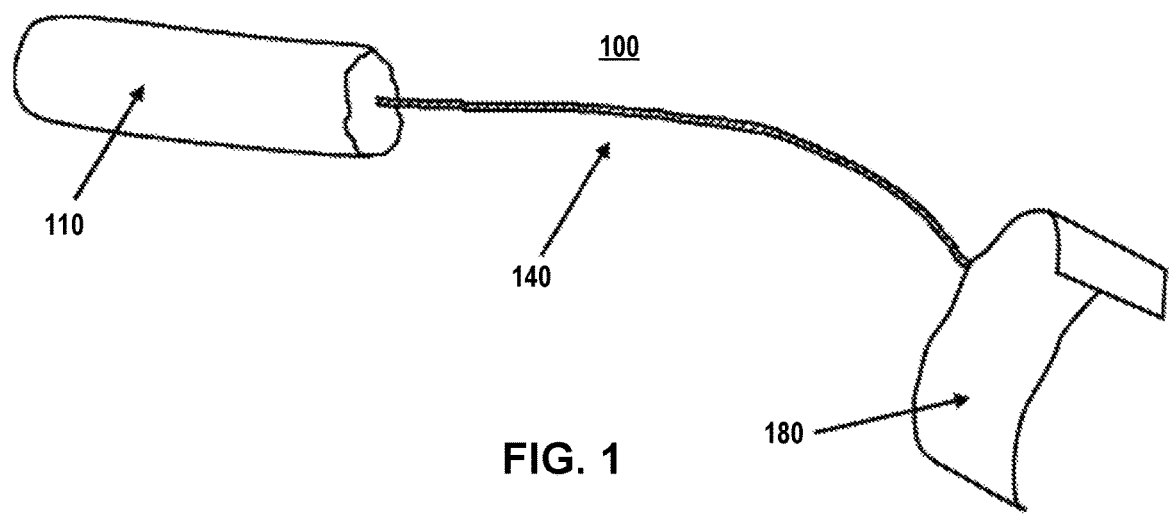
FIG. 1 depicts one preferred embodiment of a secure tampon 100 according to the present invention.

Although the detailed description herein contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention. While embodiments are described in connection with the drawings and related descriptions, there is no intent to limit the scope to the embodiments disclosed herein. On the contrary, the intent is to cover all alternatives, modifications, and equivalents. In alternate embodiments, additional devices, or combinations of illustrated devices, may be added to, or combined, without limiting the scope to the embodiments disclosed herein.

As used herein, the phrases "in one embodiment," "in various embodiments," "in some embodiments," and the like are used repeatedly. Such phrases do not necessarily refer to the same embodiment. The terms "comprising," "having," and "including" are synonymous, unless the context dictates otherwise.

Unless defined otherwise, all technical terms used herein have the same meaning as commonly understood by one of ordinary skill in the art.

As used herein, the term "secure tampon" is understood, in accordance with the present invention, to refer to any absorbent object which is securely attached to at least one or more connector elements, and further wherein the one or more connector elements are, in turn, safely and securely attached to at least one or more adhesive elements. The one or more adhesive elements comfortably, securely, safely and reversibly attach to at least one area of the tampon wearer's body including but not limited to any area of skin surrounding the vagina, any part of the leg (or legs), inner thigh, or any area of the skin covering the pubic bone, and preferably as close as possible to the labia, but still outside of the labia.

According to one preferred embodiment of the present invention, a secure tampon is provided that includes at least one adhesive means for attaching the secure tampon to at least one area of a woman's body. One such preferred adhesive means for attaching the tampon to at least one area of a woman's body is the use of tape or other adhesive material that is attached to at least one or more connector elements.

The secure tampon of the present invention can be worn during any period of time, including but not limited to any time during a woman's menstrual cycle, when any amount of blood is in contact with the tampon, as well as when the tampon is substantially saturated or completely saturated. Use of the secure tampons of the present invention allows the wearer of the tampon to prevent loss of the tampon during use and address and overcome other disadvantages of conventional, non-secure tampons.

It is to be understood that females of any suitable age can use the secure tampons of the present invention. This includes, but is not limited to, young women who are starting to experience menstrual cycles or menstruation, women of any age who are already experiencing menstrual cycles or menstruation, and women in perimenopause. The secure tampons of the present invention will preferably be used by women from the age of menstruation to menopause, who either use tampons or who have never before used tampons because of concerns and problems associated with the use of conventional, non-secure tampons.

The terms "female" and "woman" and "women" may be used interchangeably herein in this description.

As used herein, the term "absorbent object" is intended to include, but is not limited to, any object that functions as a tampon, such as a plug or other mass of soft material, which can be safely inserted into a female's vagina to absorb menstrual blood, e.g., during a menstrual period. The absorbent object of the present invention can be made of any suitable material including, but not limited to, cotton, rayon, a blend of cotton and rayon, or any other suitable material or blend of materials. The absorbent object of the present invention can also include any organic material or combination of organic materials, such as for example materials in an "organic" tampon.

As used herein, the term "absorbent" is intended to include any degree of absorbency, including but not limited to partial absorbency, substantial absorbency or complete absorbency, wherein "absorbency" refers to the ability of the absorbent object to absorb or soak up menstrual blood, e.g., during a menstrual period.

In accordance with the present invention, one preferred embodiment of an absorbent object is an applicator tampon which generally expands axially (i.e., increases in length) when inserted into the vagina of the tampon wearer.

In accordance with the present invention, another preferred embodiment of an absorbent object is a tampon which generally expands radially (i.e. increases in diameter) when inserted into the vagina of the tampon wearer.

The secure tampon of the present invention may be scented or unscented, and can have any desired size, shape and dimensions, and can be designed to have any color (or combination of colors) as well as have any desired thickness. One example of a secure tampon may be a cylinder-like shape, so it can be easily inserted into the opening of the vagina. The secure tampon absorbs a woman's menstrual flow, or blood, before the menstrual flow has a chance to leave the body. The secure tampons may come in different sizes and have different absorbencies.

Moreover, females can use the secure tampons of the present invention when wearing any kind of panties, including but not limited to strapless panties, thong panties, and other type of female panties. A female can use the secure tampon for any suitable period of time, but it is recommended not use tampons for more than eight hours.

In accordance with the present invention, examples of at least one or more connector elements include, but are not limited to, any type of safe and non-toxic string, thread, filament, fiber, microfiber, yarn or other type of safe and non-toxic connective element. Examples of representative materials that can be used to form safe and non-toxic connective elements include, but are not limited to, safe and non-toxic types of thread, cotton, rubber or plastic. Preferably the safe and non-toxic connective elements are elongated and resistant to tearing.

In accordance with the present invention, examples of at least one or more adhesive elements include, but are not limited to, any type of safe and non-toxic tape, adhesive material, such as waterproof tape, medical adhesive tape, pressure sensitive adhesive tape, surgical tape, paper tape, or any combination thereof, and can be made of any number of different types of materials, such as for example, cloth, waterproof material, paper, pressure-sensitive tape, micropore adhesive material, or any combination thereof, to name just a few examples.

An adhesive element (for instance, a piece of tape) can have any desired or suitable size, shape and dimensions. By way of non-limiting example, an adhesive element can have any one of the following representative dimensions listed below (all numbers shown below are given in inches, and indicate representative dimensions of a representative adhesive element):

1. 1.5"×3"
2. 1.5"×3"
3. 1.5"×3"
4. 1"×2.5"
5. 1"×2.5"
6. ¾"×3"
7. ¾"×3"
8. $^{11}/_{16}$"×2.5"
9. $^{11}/_{16}$"×2.5"
10. 1.25"×2"

The secure tampons of the present invention will significantly help prevent loss of a tampon during use by a woman, and also significantly help to prevent associated health and medical problems associated with a lost tampon (such as, for example, loss of a tampon due to loss of the string attached to the tampon). The secure tampons of the present invention may be useful in helping to prevent toxic shock syndrome (TSS).

As discussed herein, most conventional, non-secure tampons have a string, however with conventional, non-secure tampons there is no adhesive element that is attached to the string. Therefore, with conventional, non-secure tampons, the string is sometimes lost, for instance when the string gets stuck or trapped or lodged within the vagina. This loss of the string is very problematic and dangerous to the woman's health. The use of a conventional, non-secure tampon is therefore often associated with many significant problems for women, including but not limited to toxic shock syndrome (TSS), a life-threatening disease. In addition to TSS, the use of conventional, non-secure tampons can also cause, or be associated with, other serious problems including, but not limited to, urinary tract infections, urogenital infections, vaginal ulcers and unwanted mucosal changes, each of which can be very detrimental. Lost tampons can also cause anxiety in women as treatment for lost tampons can occur not only with an OBGYN, but also at emergency rooms and urgent care centers.

In accordance with the present invention, the adhesive element (e.g. soft tape) on the secure tampon secures the tampon to at least one part of a woman's body, so she sees it and will not forget about it or lose the string inside her. Thus, the secure tampon of the present invention reduces the risk of contracting TSS and other complications, and also reduces the risk of urinary tract infections, urogenital infections, vaginal ulcers and unwanted mucosal changes. The secure tampon of the present invention also offers improved hygiene because the string will not get lost near the behind, thus minimizing *e-coli* bacterial infections. The adhesive element (e.g. soft tape) functions like an anchor to the body so a woman wearing it does not lose the tampon or forget about it. Further, some women complain about the string getting caught on underwear or clothing and causing the tampon to shift while walking and even get tugged out while walking. Other women do not like how the string can hang out of a bikini, underwear or skirt, all of which can be embarrassing. To prevent the string hanging out, some women cut the string shorter, but then become even more concerned about losing it with the shorter string. Also, some menstruating women inquire about being able to have sex with a tampon to prevent a bloody mess. The secure tampon can enable sex without a mess because the tape or other adhesive element (when adhered to a part of the woman's body) keeps the tampon intact.

Prior to the present invention, there has been no solution for preventing the loss of a tampon and there have been no tampons that allow a woman to securely tape or otherwise attach or securely fix the tampon to her body. Prior to the present invention, there have been no preventive measures that enable a woman to reliably prevent the loss of her tampon.

The secure tampon of the present invention is a revolutionary product for the feminine hygiene market. The secure tampon of the present inventions enables younger women, especially pubescent girls who are afraid to use tampons or whose parents might not allow it, use tampons.

According to one embodiment, the present invention encompasses an already self-assembled secure tampon with tape attached to the string that is already assembled and ready to use. By way of non-limiting example, a woman can purchase a package that includes an already self-assembled secure tampon (or, alternatively, a package containing multiple self-assembled secure tampons) with or without applicators. Moreover, each already self-assembled secure tampon can be designed either with or without an applicator, thus giving consumers more options. In a preferred embodiment, in which each already self-assembled secure tampon is designed without an applicator, each of the already self-assembled secure tampons includes an absorbent object (such as, for example, an organic tampon) which is already securely attached to at least one or more connector elements, and further wherein the one or more connector elements are, in turn, safely and securely attached to at least one or more adhesive elements.

According to another embodiment, the present invention encompasses a "do-it-yourself" kit for self-assembly of a secure tampon, either with or without an applicator, thus giving consumers more options. In a preferred embodiment, a "do-it-yourself" kit for self-assembly of a secure tampon (in one case, without an applicator) includes an absorbent object (such as, for example, an organic tampon), which is already securely attached to at least one or more connector elements. The "do-it-yourself" kit also separately includes at least one or more adhesive elements (two pieces of tape that a woman can use with any tampon with a string). When someone purchases the kit, they can very easily securely attach the one or more adhesive elements to the at least one or more connector elements, wherein the one or more connector elements are already securely attached to the absorbent object.

According to yet another embodiment, the present invention encompasses another type of "do-it-yourself" kit that includes just one or two adhesive elements. By way of non-limiting example, when a woman purchases this kit, she can very easily attach the one or two adhesive elements to one of her own tampons, e.g., by securely attaching the one or more adhesive elements to a string that is already attached to the tampon. In this manner, she can form her own secure tampon for safe, secure and reliable use.

According to one preferred embodiment, shown in FIG. 1, a secure tampon 100 comprises an absorbent object 110 (the absorbent object 110 is shown on the left side of FIG. 1) which is securely attached to at least one or more connector elements 140 (e.g., the connector elements in FIG. 1 are the cords or strings), and further wherein the one or more connector elements 140 are, in turn, safely and securely attached to at least one or more adhesive elements 180 (the adhesive element 180 is the piece of flexible tape which is shown on the right side of FIG. 1). The one or more adhesive elements 180 (i.e. the piece of flexible tape which is shown on the right side of FIG. 1) comfortably, securely, safely and reversibly attach to at least one area of the tampon wearer's body.

Figure 2:
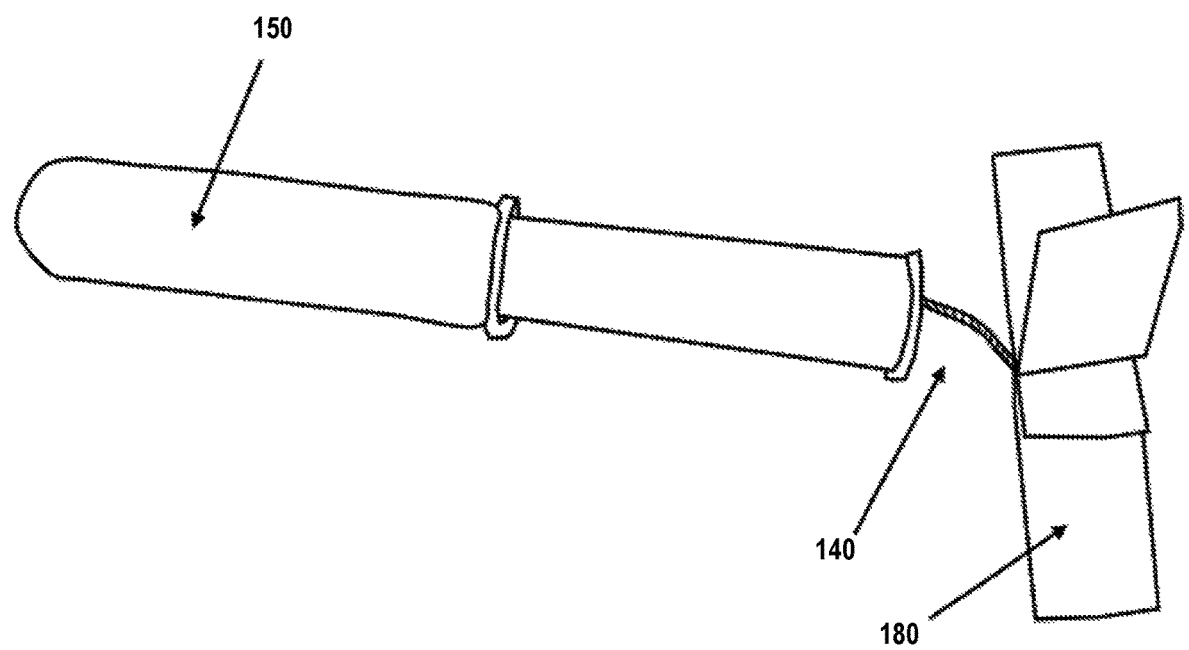
FIG. 2 depicts one preferred embodiment of a secure tampon with an applicator 150.

It is to be understood that, in accordance with the present invention, secure tampons can be used with or without an applicator, such as a built-in applicator. Referring to FIG. 2, many women may prefer to use a secure tampon 100 with an applicator 150. Any suitable applicator can be used to place the secure tampon 100. In a preferred embodiment, the present invention includes an absorbent object 110 itself that a woman inserts into her vagina, and an applicator 150 (e.g. a plastic applicator) that the woman uses to insert the absorbent object 110 in her vaginal opening. In one example, after a woman washes her hands, the woman places the absorbent object 110 in her vaginal opening. One such example of a secure tampon 100 with an applicator 150, in accordance with the present invention, is shown in FIG. 2.

According to a preferred embodiment, the secure tampon 100, which comprises an absorbent object 110, is securely attached to at least one or more connector elements 140. By way of example, the connector elements 140, as shown in FIG. 1 and FIG. 2, can include one or more cords or strings, or other type of connecting material. The one or more connector elements 140 are, in turn, safely and securely attached to at least one or more adhesive elements 180. By way of example, the adhesive elements 180 are shown on the right side of FIG. 1 and FIG. 2. The one or more adhesive elements 180 comfortably, securely, safely and reversibly attach to at least one area of the tampon wearer's body.

Figure 3:
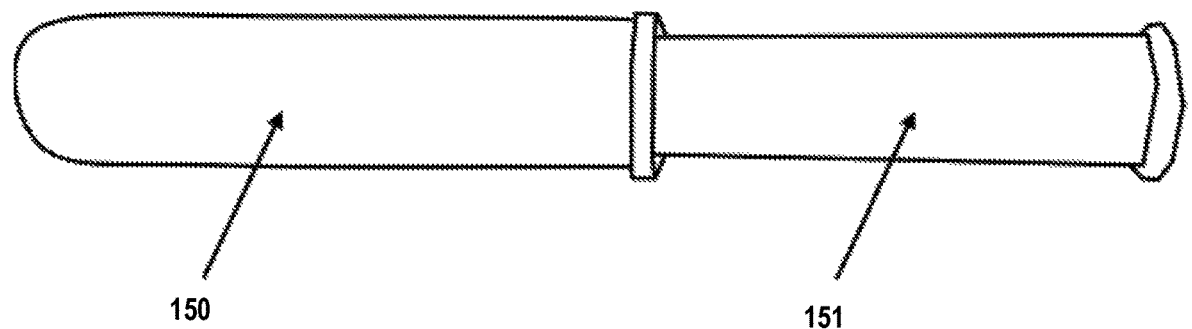
FIG. 3 depicts one preferred embodiment wherein the elements of a secure tampon are conveniently stored within the applicator 150.

According to one preferred embodiment, the connector elements 140 and adhesive elements 180 can be conveniently stored within the applicator 150, as shown by way of example in FIG. 3. As depicted in FIG. 3, the connector elements 140 and adhesive elements 180 are not visible because the connector elements 140 and adhesive elements 180 are conveniently rolled up inside the right side 151 of the applicator.

Figure 4:
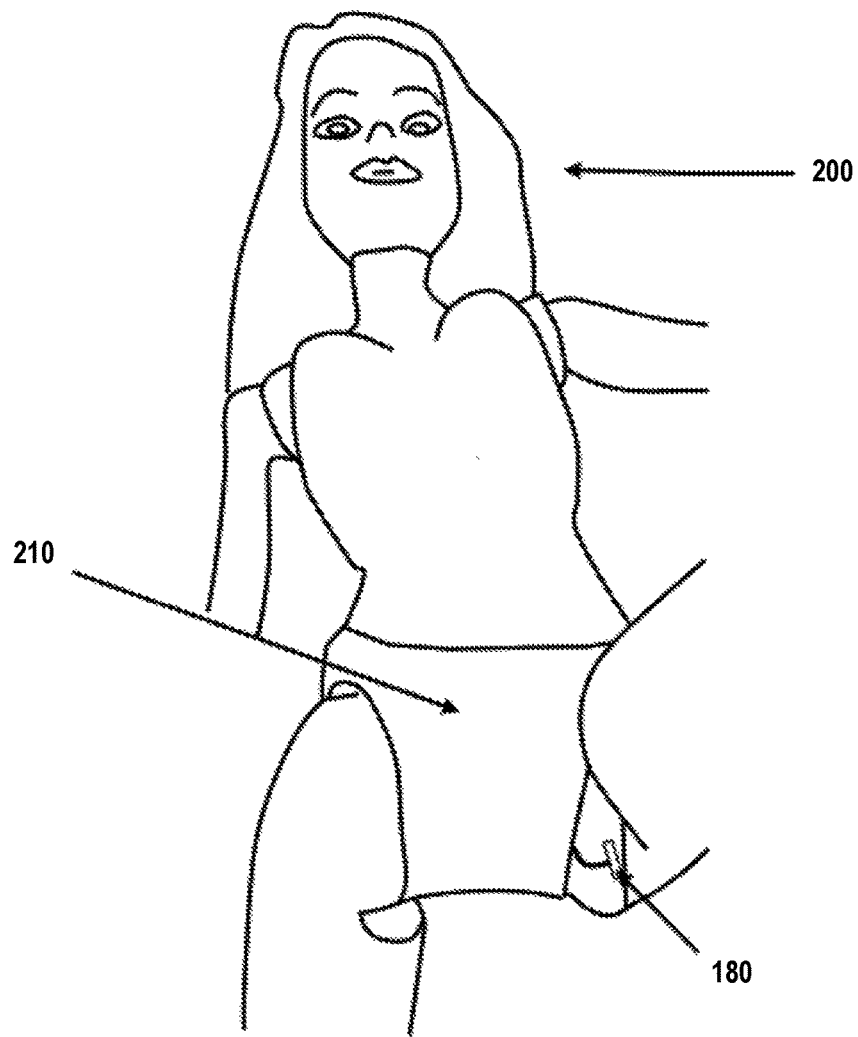
FIG. 4 depicts one embodiment of a woman wearing panties after application of a secure tampon of the invention.

By way of non-limiting example, referring to FIG. 4, after a woman 200 wearing panties 210 has inserted an absorbent object 110 into the opening of her vagina, she then safely, securely and reversibly places the one or more adhesive elements 180 to the skin surrounding her vagina, as shown by the adhesive element 180 that the woman has adhered to the skin surrounding her vagina, as shown in FIG. 4.

Figure 5:
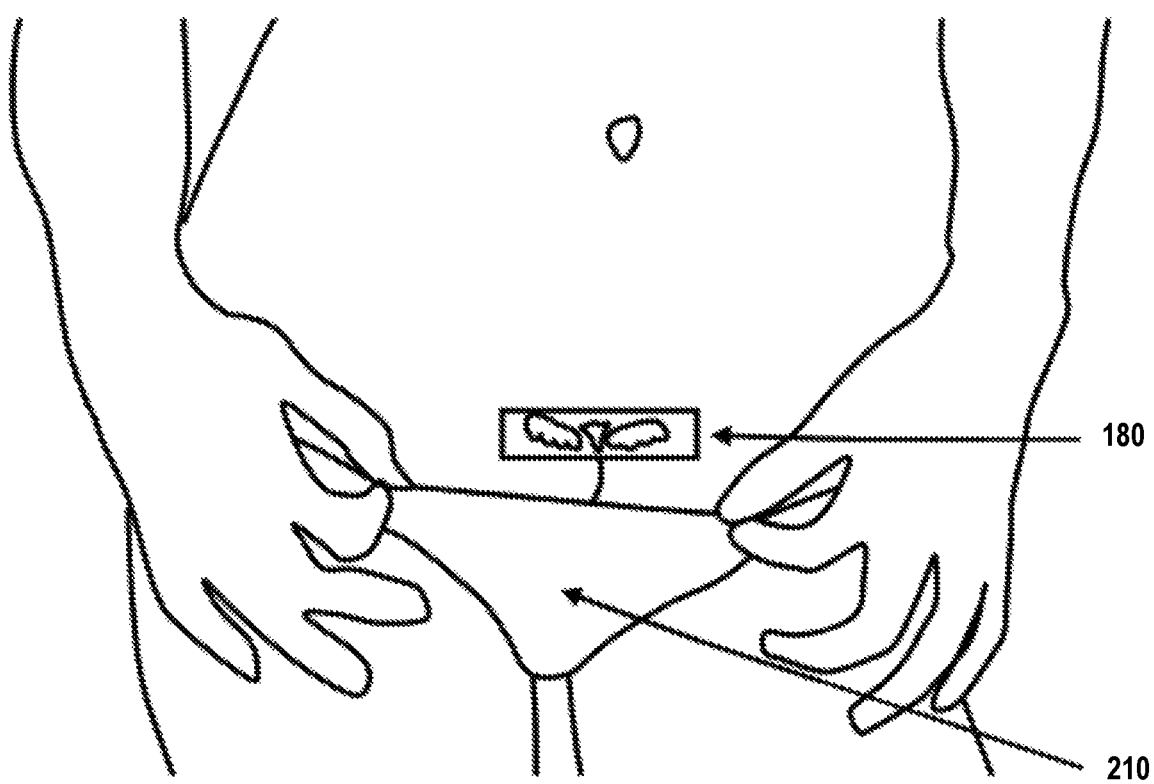
FIG. 5 shows a representative close-up view of the mid-region of a woman wearing panties after applying a secure tampon of the present invention.

Also, by way of non-limiting example, FIG. 5 shows a representative close-up view of the mid-region of a woman 200 wearing panties 210 after applying a secure tampon 100 of the present invention.

As shown in FIG. 5, the woman has safely, securely and reversibly adhered an adhesive element 180 to the skin surrounding her vagina. This is shown, by way of example, by the adhesive tape (one example of an adhesive element 180) that the woman has adhered to her skin, as shown in FIG. 5. An adhesive element 180 can also have any aesthetic design, as shown by the design on the tape shown in FIG. 5.

As shown in FIG. 5, the adhesive element (for instance, soft tape) on the secure tampon secures the tampon to a woman's body, and she therefore also sees the adhesive element and will not forget about it or lose the string (or other connective element) inside her. The secure tampon of the present invention also offers improved hygiene because the string will not get lost near the behind, possibly minimizing *E. coli* bacterial infections.

Example of Use of a Secure Tampon

1) A woman inserts an absorbent object into her vagina to absorb menstrual blood, wherein the absorbent object is securely attached to a string, and further wherein the string is, in turn, securely attached to at least one piece of pressure sensitive adhesive tape.

2) The woman peels off the back of the pressure sensitive adhesive tape.

3) The woman then places the pressure sensitive adhesive tape onto either her inner thigh or pubic bone, as close as possible to the labia, but obviously outside of it.

4) When the woman is ready to remove the absorbent object, she simply just unpeels the pressure sensitive adhesive tape and removes the absorbent object out and t discards it.

The foregoing descriptions of the embodiments of the present invention have been presented for purposes of illustration and description. They are not intended to be exhaustive or to limit the present invention to the precise forms disclosed. Although specific embodiments have been illustrated and described herein, a variety of alternate and/or equivalent implementations may be substituted for the specific embodiments shown and described without departing from the scope of the present disclosure. This application is intended to cover any adaptations or variations of the embodiments discussed herein.

The invention claimed is:

1. A secure tampon, comprising:
   an absorbent object which is securely attached to at least one or more connector elements, wherein the at least one or more connective elements are elongated and resistant to tearing, further wherein the one or more connector elements are safely and securely attached to at least one or more adhesive elements, wherein the adhesive elements are attached and anchored to a female body
   wherein the at least one or more adhesive elements comprised of any type of safe and non- toxic tape, adhesive material, waterproof tape, medical adhesive tape, pressure sensitive adhesive tape, surgical tape, paper tape, cloth, waterproof material, paper, pressure-sensitive tape, micropore adhesive material, or any combination thereof,
   further wherein each of the at least one or more adhesive elements is 1.5 inches by 3 inches in dimension, 1 inch by 2.5 inches in dimension, ¾ inch by 3 inches in dimension, 11/16 inches by 2.5 inches in dimension, or 1.25 inches by 2 inches in dimension, further wherein at least one or more adhesive elements securely and reversibly attach to any area of skin surrounding a vagina, any part of the upper leg, inner thigh, or any area of skin covering a pubic bone, outside of the labia, further wherein an aesthetic design is present on the at least one or more adhesive elements, wherein the absorbent object is made of a material selected from the group consisting of cotton, rayon, and a blend of cotton and rayon, further wherein the absorbent object comprises an organic material or combination of organic materials further wherein the at least one or more connector elements comprises any type of safe and non-toxic string, thread, filament, fiber, microfiber, yarn or other type of safe and non-toxic connective element, further wherein the tampon expands radially when inserted into the vagina, further wherein the tampon enables sex because at least one or more of the adhesive elements to keep the tampon intact and anchored to the female body, further wherein the least one or more connector elements and the at least one or more adhesive elements are stored within an applicator, further wherein the secure tampon helps to prevent toxic shock syndrome and also reduces the risk of urinary tract infections, urogenital infections, vaginal ulcers and unwanted mucosal changes.

2. The secure tampon of claim 1, wherein the secure tampon is scented.

3. The secure tampon of claim 1, wherein the secure tampon is unscented.

4. The secure tampon of claim 1, wherein the secure tampon minimizes e-coli bacterial infections.

* * * * *